United States Patent [19]

Petuch et al.

[11] Patent Number: 4,997,849

[45] Date of Patent: Mar. 5, 1991

[54] MICROBIAL TRANSFORMATION OF SIMVASTATIN

[75] Inventors: Brian R. Petuch, Florence; Byron H. Arison, Watchung, both of N.J.

[73] Assignee: Merck & Co., Inc., Rahway, N.J.

[21] Appl. No.: 370,481

[22] Filed: Jun. 23, 1989

[51] Int. Cl.⁵ .................. A61K 31/365; C07D 309/30
[52] U.S. Cl. .................................. 514/460; 549/292; 514/824
[58] Field of Search ................ 549/292; 514/460, 824

[56] References Cited

U.S. PATENT DOCUMENTS

| | | | |
|---|---|---|---|
| 3,983,140 | 9/1976 | Endo et al. | 549/292 |
| 4,255,444 | 3/1981 | Oka et al. | 549/292 |
| 4,448,979 | 5/1984 | Terahara et al. | 549/292 |
| 4,517,373 | 5/1985 | Terahara et al. | 549/292 |
| 4,537,859 | 8/1985 | Terahara et al. | 435/146 |
| 4,795,811 | 1/1984 | Grohm et al. | 549/292 |

FOREIGN PATENT DOCUMENTS

20750134 4/1981 United Kingdom ................ 549/292

*Primary Examiner*—Richard L. Raymond
*Assistant Examiner*—Mark W. Russell
*Attorney, Agent, or Firm*—Melvin Winokur; Joseph F. DiPrima

[57] ABSTRACT

Compounds of formula (I) and (II):

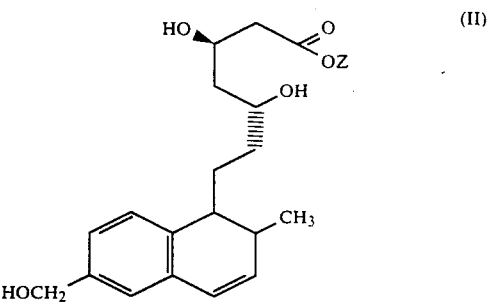

are HMG-CoA reductase inhibitors.

3 Claims, No Drawings

MICROBIAL TRANSFORMATION OF SIMVASTATIN

BACKGROUND OF THE INVENTION

Hypercholesterolemia is known to be one of the prime risk factors for atherosclerosis and coronary heart disease, the leading cause of death and disability in western countries. The bile acid sequestrants seem to be moderately effective as antihypercholesterolemic agents but they must be consumed in large quantities, i.e., several grams at a time, and they are not very palatable.

MEVACOR® (lovastatin), now commercially available, is one of a group of very active antihypercholesterolemic agents that function by limiting cholesterol biosynthesis by inhibiting the enzyme, HMG-CoA reductase. In addition to the natural fermentation products, mevastatin and lovastatin, there are a variety of semi-synthetic and totally synthetic analogs thereof. For example, simvastatin wherein the 8-acyl moiety is 2,2-dimethylbutyryl is an even more potent HMG-CoA reductase inhibitor than lovastatin.

The naturally occurring compounds and their semi-synthetic analogs have the following general structural formulae:

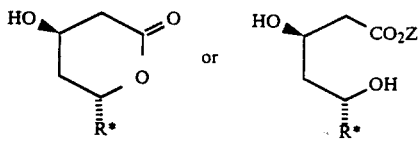

wherein:
Z is hydrogen, $C_{1-5}$ alkyl or $C_{1-5}$ alkyl substituted with a member of the group consisting of phenyl, dimethylamino, or acetylamino; and
R* is:

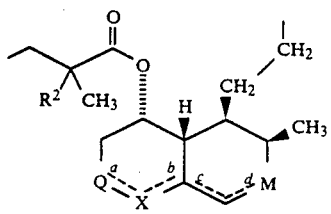

wherein Q is

or $R^3$—CH; $R^3$ is H or OH;
M is

$R^4$ is hydrogen or hydroxy;
X is $CR^5R^6$, O, S, or NH; $R^5$ and $R^6$ are H, OH, or $OR^7$ where $R^7$ represents a phosphoryl or acyl moiety;
$R^2$ is hydrogen or methyl; and a, b, c, and d represent single bonds, one of a, b, c or d represents a double bond, or both a and c or both b and d represent double bonds provided that when a is a double bond, Q is

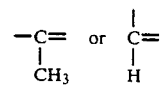

and when d is a double bond, M is

and provided that when $R^5$ or $R^6$ is OH or $OR^7$ or X is O, S, or NH, a, b, and c are single bonds.

U.S. Pat. No. 4,517,373 discloses semi-synthetic hydroxy containing compounds represented by the above general formula wherein R* is

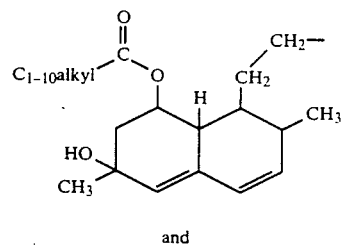

and

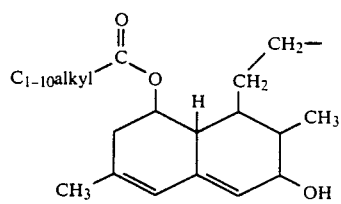

U.S. Pat. No. 4,537,859 U.S. Pat. No. 4,448,979 also disclose semi-synthetic hydroxy-containing compounds represented by the above general formula wherein R* is

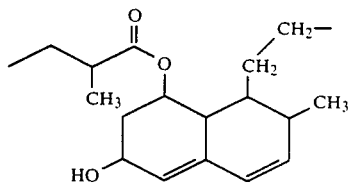

and

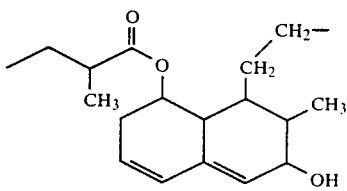

These compounds are prepared by the action of certain microorganisms on the corresponding non-hydroxylated substrates. One such organism described in U.S. Pat. No. 4,537,859 is of the genus Nocardia.

Copending U.S. patent application Ser. No. 213,010 filed June 29, 1988 discloses 5-oxygenated compounds of the above formula wherein R* is:

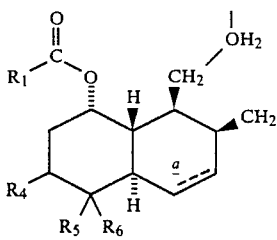

wherein $R_5$ and $R_6$ independently are H, OH or an oxygenated derivative $OR_7$ provided that one and only one of $R_5$ and $R_6$ is OH or $OR_7$.

Copending U.S. patent application Ser. No. (250,646) filed Sept. 29, 1988 discloses a chemical methodology to the 5-oxygenated compounds described above.

British patent No. GB 2,075,013 discloses compounds of the above formula wherein R* is:

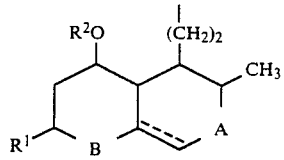

wherein A amongst other groups is C=O, B amongst other groups is —$CHOR^3$ in which $R^3$ represents an H or a acyl group, $R^1$ is an H or a methyl group and $R^2$ is an H or a acyl group. The 3-keto, 5-hydroxy compound in this disclosure is formed in minor amounts from a chemical oxidation of the hexahydro starting material.

DETAILED DESCRIPTION OF THE INVENTION

The present invention relates to compounds of formula (I) and (II):

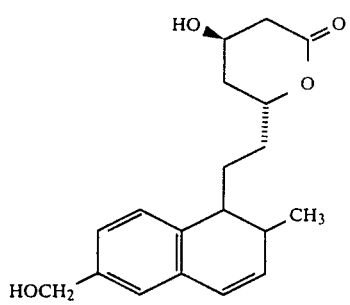

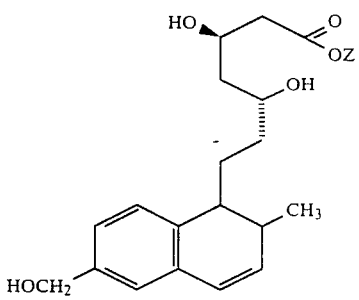

wherein: Z is H, $C_{1-5}$alkyl, or $C_{1-5}$alkyl substituted with a member of the group consisting of phenyl, dimethylamino or acetylamino; and pharmaceutically acceptable salts of the compounds of formula (II) in which Z is hydrogen.

Compound (I) is prepared in a microbial transformation from simvastatin employing a novel microorganism (MA 6559) tentatively identified as an Actinoplanacete sp. The process involves the bioconversion of substrate (II) with the microorganism MA 6559.

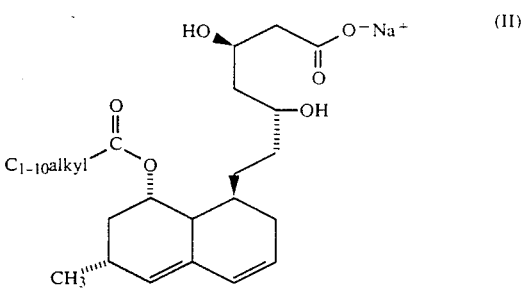

The acyl moiety

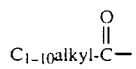

can be branched or straight, preferably it is 2-methylbutyryl or 2,2-dimethylbutyryl, most preferably 2,2-dimethylbutyryl.

The characteristics of microorganism MA 6559 tentatively identified as Actinoplanacete sp. are described below:

Microscopic observations—Culture grows as branched filaments ranging of approximately 6 microns diameter. Spherical to ovoid sporangia are detected on glycerolasparagine agar, oatmeal agar, yeast-malt extract agar and inorganic salts-starch agar. Sporangia range in size from 2.5-44 microns in diameter.

Oat Meal Agar

Vegetative Growth: Reverse is hyaline
Aerial Mass: Moderate, off white, powdery
Soluble Pigment: None Glycerol-Asparagine Vegetative Growth: Obverse is mahogany
Aerial Mycelium: Off white and cottony at periphery turning to dusty rose and powdery at colony center
Soluble Pigment: Very light brown

Inorganic Salts-Starch Agar

Vegetative Growth: Mahogany
Aerial Mycelium: Off white and cottony at periphery turning to dustry rose and powdery at colony center
Soluble Pigment: Areas of browning around the periphery of growth with slight clearing of starch

Yeast Extract-Malt Extract Agar

Vegetative Growth: Mahogany to brown black
Aerial Mass: Isolated areas of white, cottony growth against a powdery dusty rose colored mycelial matte
Soluble Pigment: Yellow-brown

Egg Albumin Agar

Vegetative Growth: Pale yellow, flat
Aerial Mass: Sparse, white and cottony limited to periphery of growth
Soluble Pigment: None

Nutrient Tyrosine Agar

Vegetative Growth: Transparent to pale yellow Aerial Mass: None
Soluble Pigment: None
Decomposition of tyrosine: Negative

Skim Milk Agar

Vegetative Growth: Leathery and yellow
Aerial Mass: Sparse, off white and powdery
Soluble Pigment: None
Hydrolysis of casein: Positive

Tomato Paste Oatmeal Agar

Vegetative Growth: Orange-yellow, rugose
Aerial Mass: Powdery, varying in color from off white to purple-brown

Gelatin Stabs

Vegetative Growth: Orange yellow
Aerial Mass: None
Soluble Pigment: None
Liquification of gelatin: Positive

Peptone-Iron-Yeast Extract Agar Slants

Vegetative Growth: Colorless, leathery
Aerial Mass: Moderate, off white, powdery
Soluble Pigment: None
Melanin: Negative
$H_2S$: Negative

Tryptone Yeast Extract Broth

Soluble Pigment: None

| Carbohydrate utilization pattern | | | | | |
|---|---|---|---|---|---|
| d-glucose | ++ | d-maltose | + | sucrose | +/− |
| d-arabinose | ++ | d-mannitol | ++ | d-xylose | ++ |
| l-arabinose | ++ | d-mannose | ++ | l-xylose | − |
| d-fructose | ++ | l-mannose | − | alpha d-lactose | ++ |
| l-glucose | +/− | d-raffinose | ++ | beta d-lactose | ++ |
| inositol | + | l-rhamnose | − | | |

Carbon source utilization studies were carried out using Pridham and Gottlieb basal medium supplemented with 1% carbon source. Scoring was graded according to the methods described in "Methods for Characterization of Streptomyces species", IJSB 16: pps 313–340.

Culture is tentatively identified as an Actinoplanaces sp.

The compound of this invention is useful as an antihypercholesterolemic agent for the treatment of arteriosclerosis, hyperlipidemia, familial hypercholesterolemia and like diseases in humans. It may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 2 mg to 2000 mg (preferably 2 to 100 mg) which may be given in two to four divided doses. Higher doses may be favorably employed as required.

The compound of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl(3-trimethylaminopropyl) iminotrimethylene dihalide]. The relative amounts of the compounds of this invention and these polymers is between 1:100 and 1:15,000.

The intrinsic HMG-CoA reductase inhibition activity of the claimed compounds is measured in the in vitro protocol described in J. Med. Chem., 1985, 28, page 347.

The compound of the formula (II), wherein R is hydrogen as the potassium salt, exhibited an $IC_{50}$ of 0.30 μg/ml in the above-referenced protocol.

Included within the scope of this invention is the method of treating arteriosclerosis, familal hypercholesterolemia or hyperlipidemia, which comprises administering to a subject in need of such treatment a nontoxic therapeutically effective amount of the compounds of formulae (I) or (II) or pharmaceutical compositions thereof.

The compound (I) is prepared in the instant process from the sodium salt of simvastatin, lovastatin or an analog having a 6-methyl group by one of the following methods:

(a) adding the substrate to a growing culture Actinoplanacete sp. for a suitable incubation period followed by isolation and derivatization, if desired;

(b) collecting a culture of the bioconverting microorganism and contacting the collected cells with the substrate.

Cultivation of the bioconverting microorganism MA 6559 tentatively identified as a Actinoplanacete sp. can be carried out by conventional means in a conventional culture medium containing nutrients well known for use with such microorganisms. Thus, as is well known, such culture media contain sources of assimilable carbon and of assimilable nitrogen and often inorganic salts. Examples of sources of assimilable carbon include glucose, sucrose, starch, glycerin, millet jelly, molasses and soybean oil. Examples of sources of assimilable nitrogen include soybean solids (including soybean meal and soybean flour), wheat germ, meat extracts, peptone, corn steep liquor, dried yeast and ammonium salts, such as ammonium sulphate. If required, inorganic salts, such as sodium chloride, potassium chloride, calcium carbonate or phosphates, may also be included. Also, if desired, other additives capable of promoting the production of hydroxylation enzymes may be employed in appropriate combinations. The particular cultivation technique is not critical to the process of the invention and any techniques conventionally used for the cultivation of microorganisms may be employed with the present invention. In general, of course, the techniques employed will be chosen having regard to industrial efficiency. Thus, liquid culture is generally preferred and the deep culture method is most convenient from the industrial point of view.

Cultivation will normally be carried out under aerobic conditions and at a temperature within the range from 20° to 37° C., more preferably from 26° to 28° C.

Method (a) is carried out by adding the substrate to the culture medium in the course of cultivation. The precise point during the cultivation at which the starting compound is added will vary depending upon the cultivation equipment, composition of the medium, temperature of the culture medium and other factors, but it is preferably at the time when the hydroxylation capacity of the microorganism begins to increase and this is usually 1 or 2 days after beginning cultivation of the microorganism. The amount of the substrate added is preferably from 0.01 to 5.0% by weight of the medium, more preferably from 0.05 to 0.5%, e.g., from 0.05 to 0.1% by weight. After addition of the substrate, cultivation is continued aerobically, normally at a temperature within the ranges proposed above. Cultivation is normally continued for a period of from 1 to 2 days after addition of the substrate.

In method (b), cultivation of the microorganism is first carried out under conditions such as to achieve its maximum hydroxylation capacity; this capacity usually reaches a maximum between 4 and 5 days after beginning the cultivation, although this period is variable, depending upon the nature and temperature of the medium, the species of microorganism and other factors. The hydroxylation capacity of the culture can be monitored by taking samples of the culture at suitable intervals, determining the hydroxylation capacity of the samples by contacting them with a substrate under standard conditions and determining the quantity of product obtained and plotting this capacity against time as a graph. When the hydroxylation capacity has reached its maximum point, cultivation is stopped and the microbial cells are collected. This may be achieved by subjecting the culture to centrifugal separation, filtration or similar known separation methods. The whole cells of the cultivating microorganism thus collected, preferably, are then washed with a suitable washing liquid such as physiological saline or an appropriate buffer solution.

Contact of the collected cells of the microorganism MA 6559 with the substrate is generally effected in an aqueous medium, for example, in a phosphate buffer solution at a pH value of from 5 to 9. The reaction temperature is preferably within the range from 20° to 45° C., more preferably from 25° to 30° C. The concentration of the substrate in the reaction medium is preferably within the range from 0.01 to 5.0% by weight. The time allowed for the reaction is preferably from 1 to 5 days, although this may vary depending upon the concentration of the substrate in the reaction mixture, the reaction temperature, the hydroxylation capacity of the microorganism (which may, of course, vary from species to species and will also, as explained above, depend upon the cultivation time) and other factors.

The microorganism useful in the novel process of this invention has been tentatively identified as Actinoplanacete sp. A sample of the culture designated ATCC 53771 is available in the permanent culture collection of the American Type Culture Collection at 12301 Parklawn Drive, Rockville, Md. 20852.

After completion of the conversion reaction by any of the above methods, the desired compound can be directly isolated, separated or purified by conventional means. For example, separation and purification can be effected by filtering the reaction mixture, extracting the resulting filtrate with a water-immiscible organic solvent (such as ethyl acetate), distilling the solvent from the extract, subjecting the resulting crude compound to column chromatography (for example on silica gel or alumina) and eluting the column with an appropriate eluent, especially in an HPLC apparatus.

The following examples illustrate the preparation of these compounds and, as such, are not to be construed as limiting the invention set forth in the claims appended hereto.

The composition of media employed in the following examples are listed below.

| Media | (g/L) |
|---|---|
| Seed Medium A | |
| Dextrose | 1.0 |
| Dextrin | 10.0 |
| Beef Extract | 3.0 |
| Ardamine pH | 5.0 |
| NZ Amine Type E | 5.0 |
| $MgSO_4.7H_2O$ | 0.05 |
| $K_2HPO_4$ | 0.37 |
| Adjust pH to 7.0 | |
| Add $CaCO_3$ | 0.5 |
| Transformation Medium B | |
| Mannitol | 5 |
| Glycerol | 5 |
| Hycase SF | 2 |
| Beef Extract | 1 |
| Cornsteep Liquor | 3 |
| Adjust pH to 7.0 | |

EXAMPLE 1

Preparation of 6-[2-[2-methyl, 6-hydroxymethyl-1,2-dihydronaphthyl]ethyl]-4-hydroxy-3,4,5,6-tetrahydro-2H-pyran-2-one A. Culture Conditions and Bioconversion Seed cultures were prepared in medium A (50 ml in a 250 ml 3-baffle Erlenmeyer flask). The seed flasks were incubated on a rotary shaker (220 rpm) at 27° C. for 24 hours. The transformation flasks (50 ml medium B in 250 ml Erlenmeyer flask) were inoculated with 2.5 ml of seed culture plus 1 mg simvastatin (10 mg/ml in $H_2O$) and incubated at 27° C. on a rotary shaker. After 48 hours the cells were separated by centrifugation, washed once with sterile saline and resuspended in sterile 100 mM phosphate buffer (pH 6.0) containing 1% glucose. Each flask was charged with 10 mg simvastatin (10 mg/ml in $H_2O$) and incubated for 48 hours.

Following incubation, the supernatant was extracted as described in B below.

B. Isolation and Purification

The centrifuged broth (50 ml) at pH 3 was extracted with three 25 ml portions of ethyl acetate. The ethyl acetate layers were combined, dried over sodium sulfate, and evaporated to a brown oil. The oil was dissolved in 50 ml of $CH_2Cl_2$, two drops of $CF_3COOH$ added and incubated at 50° for one hour. The reaction mixture was evaporated and the residue redissolved in acetonitrile. Further purification was obtained by HPLC on a Partisil 10 ODS-3 column developed with 45% aqueous acetonitrile. The fractions at retention time 6.13 minutes were pooled and evaporated to yield the titled compound.

H'NMR δ1.02 (d), 2.42(ddd), 2.59(dd), 4.18(m), 4.52(s), 4.52(m), 5.84(dd), 6.43(dd), 7.04(s)* 7.12(dd), 7.14(d).

Doublet structure not resolved under experimental conditions.

EXAMPLE 2

Preparation of Ammonium Salts of Compounds II

To lactone (1.0 mmol) from Example 1 Step b, in ethanol solution, is added with stirring in 0.1N NaOH (1.1 mmol) at ambient temperature. The resulting solution is cooled and acidified by the dropwise addition of 1N HCl. The resulting mixture is extracted with diethyl ether and the extract washed with brine and dried (MgSO$_4$). The MgSO$_4$ is removed by filtration and the filtrate saturated with ammonia (gas) to give the ammonium salt.

EXAMPLE 3

Preparation of Alkali and Alkaline Earth Salts of Compounds II

To a solution of 49 mg of lactone from Example 1 Step b in 2 ml of ethanol is added 1 ml of aqueous 0.1N NaOH. After one hour at room temperature, the mixture is taken to dryness in vacuo to yield the desired sodium salt.

In like manner, the potassium salt is prepared using one equivalent of potassium hydroxide, and the calcium salt, using one equivalent of Ca(OH)$_2$.

EXAMPLE 4

Preparation of Ethylenediamine Salts of Compounds II

To a solution of 0.50 g of the ammonium salt from Example 2 in 10 ml of methanol is added 0.06 ml of ethylenediamine. The methanol is stripped off under vacuum to obtain the desired ethylenediamine salt.

EXAMPLE 5

Preparation of Tris(hydroxymethyl)aminomethane Salts of Compounds II

To a solution of 202 mg of the ammonium salt from Example 2 in 5 ml of methanol is added a solution of 50 mg of tris(hydroxymethyl)aminomethane in 5 ml of methanol. The solvent is removed in vacuo to afford the desired tris(hydroxymethyl)aminomethane salt.

EXAMPLE 6

Preparation of L-Lysine Salts of Compounds II

A solution of 0.001 mole of L-lysine and 0.0011 mole of the ammonium salt from Example 2 in 15 ml of 85% ethanol is concentrated to dryness in vacuo to give the desired L-lysine salt.

Similarly prepared are the L-arginine, L-ornithine, and the α,β-diaminobutyric acid salts.

EXAMPLE 7

Preparation of Tetramethylammonium Salts of Compounds II

A mixture of 68 mg of ammonium salt from Example 2 in 2 ml of methylene chloride and 0.08 ml of 24% tetramethylammonium hydroxide in methanol is concentrated to dryness to yield the desired tetramethylammonium salt.

EXAMPLE 8

Preparation of Methyl Esters of Compounds II

To a solution of 400 mg of lactone from Example 1 Step b in 100 ml of absolute methanol is added 10 ml 0.1M sodium methoxide in absolute methanol. This solution is allowed to stand at room temperature for one hour, then is diluted with water and extracted twice with ethyl acetate. The organic phase is separated, dried (Na$_2$SO$_4$), filtered and evaporated in vacuo to yield the desired methyl ester.

In like manner, by the use of equivalent amounts of the alkoxides derived from propanol, butanol, isobutanol, t-butanol, amyl alcohol, isoamyl alcohol, 2-dimethylaminoethanol, benzyl alcohol, phenylethanol, 2-acetamidoethanol and the like, and employing the corresponding alcohol as solvent the corresponding esters are obtained.

EXAMPLE 9

Preparation of Free Dihydroxy Acids

The sodium salt of the compound II from Example 8 is dissolved in 2 ml of ethanol-water (1:1; v:v) and added to 10 ml of 0.1N hydrochloric acid from which the dihydroxy acid is extracted with ethyl acetate. The organic extract is washed once with water, dried (Na$_2$SO$_4$), and evaporated in vacuo with a bath temperature not exceeding 30° C. The dihydroxy acid derivative derived slowly reverts to the corresponding parent lactone on standing at room temperature.

EXAMPLE 10

As a specific embodiment of a composition of this invention, 20 mg of lactone from Example 1 Step b is formulated with sufficient finely divided lactose to provide a total amount of 580 to 590 mg to fill a size 0, hard-gelatin capsule.

What is claimed is:

1. A compound of formula (I)

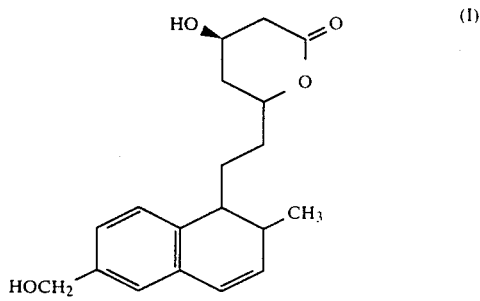

(I)

2. A hypocholesterolemic, hypolipidemic pharmaceutical composition comprising a nontoxic therapeutically effective amount of a compound of claim 1 and a pharmaceutically acceptable carrier.

3. A method of treating hypercholesterolemia comprising the administration to a subject in need of such treatment a nontoxic therapeutically effective amount of a compound of claim 1.

* * * * *